United States Patent

Barner et al.

[11] Patent Number: 4,559,407
[45] Date of Patent: Dec. 17, 1985

[54] INTERMEDIATE IN THE PRODUCTION OF VITAMIN E

[75] Inventors: Richard Barner, Witterswil; Josef Hübscher, Seon, both of Switzerland

[73] Assignee: Hoffmann-La Roche Inc., Nutley, N.J.

[21] Appl. No.: 540,253

[22] Filed: Oct. 11, 1983

[30] Foreign Application Priority Data

Oct. 27, 1982 [CH] Switzerland ............ 6270/82

[51] Int. Cl.$^4$ ........................................ C07D 303/32
[52] U.S. Cl. .................... 549/548; 549/555; 549/557; 549/215; 549/414
[58] Field of Search ............................ 549/548

[56] References Cited

FOREIGN PATENT DOCUMENTS 058945 9/1982 European Pat. Off. .

OTHER PUBLICATIONS

Cohen, Journal of Organic Chemistry, vol. 46, No. 12 (1981), pp. 2445–2450.

Primary Examiner—Norma S. Milestone
Attorney, Agent, or Firm—Jon S. Saxe; George M. Gould; William H. Epstein

[57] ABSTRACT

There is described a novel process for the manufacture of hydroquinone derivatives of the formula

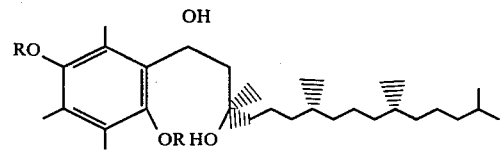

wherein R represents an ether protecting group, and their conversion into d-α-tocopherol starting from compounds of the formula

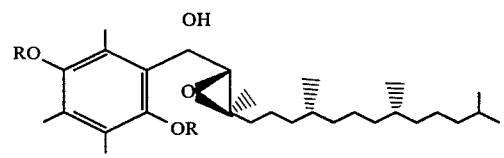

wherein R has the above significance.

1 Claim, No Drawings

INTERMEDIATE IN THE PRODUCTION OF VITAMIN E

Several processes for the manufacture of natural vitamin E are known, but technically they are only of limited interest. Accordingly, natural vitamin E has hitherto been extract almost exclusively from natural sources.

There accordingly exists a need for a technically realizable process in accordance with which natural vitamin E can be obtained in good yield and with high optical purity. This is now made possible by means of the process in accordance with the invention.

SUMMARY OF THE INVENTION

This process comprises regioselectively reducing a compound of the general formula

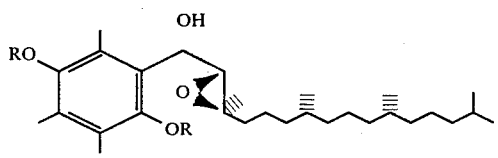   I wherein R represents an ether protecting group, if desired converting a thus-obtained compound of the general formula

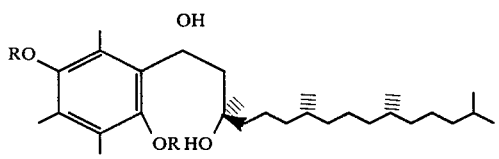   II wherein R has the above significance, into a compound of the general formula

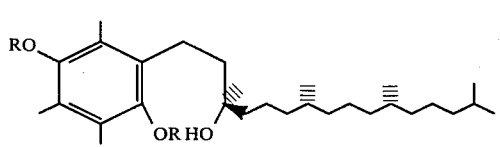   III wherein R has the above significance, and, if desired, converting the latter into d-α-tocopherol of the formula

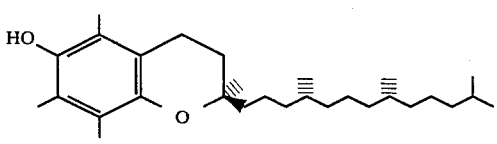   IV

DETAILED DESCRIPTION

The term "ether protecting group" signifies in the scope of the present invention not only groups cleavable by hydrolysis such as, for example, trialkylsilyl groups, alkoxyalkyl groups (e.g. the methoxymethyl group) or the tetrahydropyranyl group, but also groups cleavable oxidatively (e.g. $C_1$–$C_6$ alkyl ether groups). Furthermore, the notation " " signifies that the corresponding residue is situated above the plane of the molecule, while the notation " " signifies that the corresponding residue is situated below the plane of the molecule.

The regioselective reduction of a compound of formula I to a compound of formula II, i.e. the reductive cleavage of the epoxide, is conveniently carried out in an inert organic solvent. Especially suitable inert organic solvents are aliphatic and aromatic hydrocarbons such as, for example, pentane, hexane, benzene, toluene and the like, ethers such as diethyl ether, tert.butyl methyl ether, tetrahydrofuran and dioxan or mixtures of hydrocarbons and ethers. The solvent or the solvent mixture is preferably chosen so that the starting material is soluble therein.

In carrying out the regioselective reaction, any conventional complex metal hydride reducing agent can be utilized.

Complex metal hydrides are especially suitable reducing agents for the regioselective opening of the epoxide. Preferred complex metal hydrides are sodium bis (2-methoxy-ethoxy)aluminium hydride [Red-al ®], lithium aluminum hydride, lithium borohydride, aluminium borohydride, aluminium hydride, diborane and the like. Sodium bis(2-methoxy-ethoxy)aluminum hydride and lithium aluminium hydride are particularly preferred.

The temperature and the pressure are not critical and the regioselective reduction can be carried out readily at room temperature and normal pressure.

The conversion of a compound of formula II into a compound of formula III can be carried out in a manner known per se. The conversion is conveniently carried out by hydrogenation in acidic medium. The hydrogenation can be carried out in the presence of a usual hydrogenation catalyst (e.g. palladium, platinum and the like) in the presence or absence of a carrier material. The acid can be a mineral acid such as hydrochloric acid or sulphuric acid, perchloric acid or a carboxylic acid such as formic acid, acetic acid and the like. The temperature and the pressure are not critical and the conversion can be carried out readily at room temperature and normal pressure.

The compounds of formula III are known and can be converted into d-α-tocopherol in a known manner. This can be carried out, for example, where the group R is cleavable by hydrolysis in a simple manner by treatment with an acid. Where the group R is cleavable oxidatively, the conversion is carried out in a simple manner by treatment with, for example, cerium ammonium nitrate [(Ce(NH$_4$)$_2$(NO$_3$)$_6$] and subsequent reductive cyclization of the quinone obtained.

The compounds of formula I used as starting materials in the process in accordance with the invention are novel. They can be prepared starting from the compound of the formula

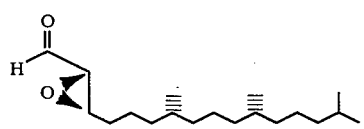   V by reaction with a compound of the general formula

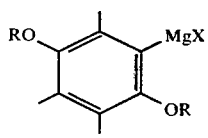

wherein R has the above significance and X represents chlorine or bromine.

This reaction can be carried out in a manner known per se, i.e. under the conditions which are usual for a Grignard reaction.

This reaction is conveniently carried out in an inert organic solvent, for example in an ether such as diethyl ether, tetrahydrofuran and the like, and at a temperature from about $-20°$ C. to about room temperature, preferably at about $-20°$ C. to about $0°$ C.

The compound of formula V above is also novel and is likewise an object of the present invention. It can be prepared in a simple manner by oxidizing the known compound of the formula

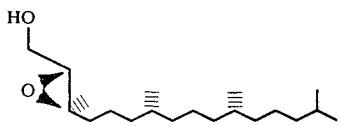

This oxidation can be carried out in a manner known per se; for example, by means of pyridinium chlorochromate in methylene chloride (Corey reagent).

The compounds of formula VI are known or are analogues of known compounds and can be prepared according to methods known per se.

The following Examples illustrate the present invention. In the Examples "Celite" is the registered Trade Mark of the Johns-Manville Corp. It is a filter aid.

EXAMPLE 1

A solution of 342 mg (0.70 mmol) of (1RS,2R,3R,7R,11R)-1-(2',5'-dimethoxy-3',4',6'-trimethylphenyl)-2,3-epoxy-3,7,11,15-tetramethylhexadecanol in 1 ml of tert.butyl methyl ether was added dropwise at room temperature while stirring to a suspension of 51 mg (2 mmol) of lithium aluminium hydride in 10 ml of tert.butyl methyl ether and the mixture was subsequently stirred at room temperature for a further 1 hour. Then, 0.5 ml of water was added dropwise, the mixture was filtered through sodium sulphate, rinsed with ether and the filtrate was concentrated on a rotary evaporator. The thus-obtained crude produce (341 mg) was chromatographed on silica gel with toluene/ethyl acetate (2:1 parts by volume) and there were obtained 284 mg (84%) of (1RS,3R,7R,11R)-1-(2',5'-dimethoxy-3',4',6'-trimethylphenyl)-3,7,11,15-tetramethylhexadecane-1,3-diol, $[\alpha]_D^{20} = +0.2°$ (c=2.16% in chloroform).

The (1RS,2R,3R,7R,11R)-1-(2',5'-dimethoxy-2',4',6'-trimethylphenyl)-2,3-epoxy-3,7,11,15-tetramethylhexadecanol used as the starting material was prepared as follows:

(A) 1.70 g (5.45 mmol) of (2R,3R,7R,11R)-2,3-epoxy-3,7,11,15-tetramethylhexadecanol in 5 ml of methylene chloride was added dropwise while stirring at room temperature to a suspension of 1.6 g (5.45 mmol) of pyridinium chlorochromate in 50 ml of methylene chloride and the mixture was stirred at room temperature overnight. Celite was then added and the mixture was stirred with 100 ml of ether for 1 hour, subsequently filtered and rinsed with ether. The crude product was chromatographed on silica gel with toluene. There was obtained 1.46 g (87%) of (2R,3R,7R,11R)-2,3-epoxy-3,7,11,15-tetramethylhexadecanal, $[\alpha]_D^{20} = -5.87°$ (c=1.5% in chloroform).

(B) 1 mmol of 2,5-dimethoxy-3,4,6-trimethylphenylmagnesium bromide in 2 ml of tetrahydrofuran was added dropwise at $0°$ C. while stirring to a solution of 300 mg (0.97 mmol) of (2R,3R,7R,11R)-2,3-epoxy-3,7,11,15-tetramethylhexadecanal in 10 ml of tetrahydrofuran. After completion of the dropwise addition, the mixture was stirred at room temperature for a further 3 hours. 20 ml of water weere then added and the mixture was extracted three times with 20 ml of ether each time. The combined organic phases were dried over sodium sulphate and concentrated on a rotary evaporator. The thus-obtained crude produce (502 mg) was chromatographed on silica gel with toluene/ethyl acetate (2:1 parts by volume) and there were obtained 448 mg(94%) of (1RS,2R,3R,7R, 11R)-1-(2',5'-dimethoxy-3',4',6'-trimethylphenyl)-2,3-epoxy-3,7,11,15-tetramethylhexadecanol, $[\alpha]_D^{20} = -0.66°$ (c=1.51% in chloroform).

EXAMPLE 2

1 ml of 70% perchloric acid was added to a solution of 197 mg (0.40 mmol) of (1RS,3S,7R,11R)-1-(2',5'-dimethoxy-3',4',6'-trimethylphenyl)-3,7,11,15-tetramethylhexadecane-1,3-diol in 20 ml of methanol and the mixture was shaken in a hydrogen atmosphere for 15 hours at room temperature in the presence of 100 mg of 10% by weight palladium/90% by weight carbon. The mixture was then neutralized with sodium carbonate, 50 ml of ethyl acetate weere added, the resulting mixture was filtered through Celite and the filtrate was concentrated on a rotary evaporator. There were obtained 165 mg (85%) of (3R,7R,11R)-1-(2',5'-dimethoxy-3',4',6'-trimethylphenyl)-3,7,11,15-tetramethylhexadecan-3ol,- $[\alpha]_D^{20} = -0.67°$ (c=0.90% in chloroform).

EXAMPLE 3

1.3 of cerium (IV) ammonium nitrate in 5 ml of water were added while stirring to a solution of 530 mg (1.13 mmol) of (3R,7R,11R)-1-(2',5'-dimethoxy-3',4',6'-trimethylphenyl)-3,7,11,15-tetramethylhexadecan-3-ol in 50 ml of acetonitrile and this mixture was stirred at room temperature for 1 hour. The mixture was extracted three times with 20 ml of methylene chloride each time, the combined organic phases were dried over sodium sulphate and evaporated on a rotary evaporator. There were obtained 480 mg of (3'R,7'R,11'R)-2-(3'-hydroxy-3',7',11',15'-tetramethylhexadecan-1'-yl-3,4,5-trimethyl-1,4-benzoquinone.

The product was dissolved in 100 ml of methanol and hydrogenated over 10% by weight palladium/90% by weight carbon. 0.5 ml of concentrated aqueous hydrochloric acid was then added and the mixture was warmed to $50°$ C. for 2 hours. The mixture was thereafter neutralized by the addition of solid sodium hydrogen carbonate and subsequently filtered; the filtrate was evaporated and the residue was chromatographed on silica gel with toluene/ethyl acetate (2:1 parts by volume). In this manner there were obtained 375 mg (90%) of 2R,4'R,8'R-α-tocopherol (d-α-tocopherol) as a pale yellowish oil. A value of 95% was determined for the optical purity of the d-α-tocopherol obtained in the above manner.
We claim:
1. The compound of the formula
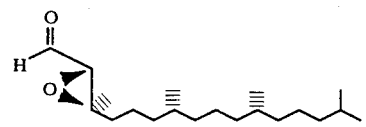
* * * * *